United States Patent [19]

Mizukami et al.

[11] Patent Number: 5,663,298
[45] Date of Patent: Sep. 2, 1997

[54] UCK14 COMPOUNDS

[75] Inventors: Tamio Mizukami; Akira Asai, both of Machida, Japan; Yoshinori Yamashita, Princeton, N.J.; Ritsuko Katahira, Yokohama, Japan; Atsuhiro Hasegawa, Machida, Japan; Keiko Ochiai, Ebina, Japan; Shiro Akinaga, Sunto-gun, Japan

[73] Assignee: Kyowa Hakko Kogyo Co., Ltd., Tokyo, Japan

[21] Appl. No.: 730,348

[22] Filed: Oct. 15, 1996

[30] Foreign Application Priority Data

Oct. 16, 1995 [JP] Japan ................. 7-267233

[51] Int. Cl.$^6$ ................. A61K 38/00; C07K 5/00; C12N 1/00; A01N 43/02
[52] U.S. Cl. ................. 530/332; 435/253.5; 549/263; 549/328
[58] Field of Search ................. 530/332; 514/19, 514/449; 549/328, 263

[56] References Cited

U.S. PATENT DOCUMENTS 5,476,952  12/1995  Su et al. ................. 548/956
5,496,808   3/1996  Bargiotti et al. ................. 514/34

*Primary Examiner*—Cecilia J. Tsang
*Assistant Examiner*—Michael Borin
*Attorney, Agent, or Firm*—White & Case

[57] ABSTRACT

The present invention relates to UCK14 compounds having antitumor activity which are represented by the formula:

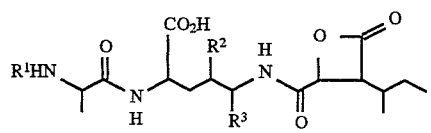

wherein $R^1$ is hydrogen or $-COOC(CH_3)_3$; and $R^2$ and $R^3$ are taken together to form $-CH_2-$, or each $R^2$ and $R^3$ independently are hydrogen, and pharmaceutically acceptable salts thereof.

5 Claims, No Drawings

UCK14 COMPOUNDS

BACKGROUND OF THE INVENTION

The present invention relates to UCK14 compounds which have antitumor activity and are useful as antitumor agents.

Heretofore, many compounds such as anthracycline compounds, anthraquinone compounds, and mitomycin compounds have been reported as antitumor substances [CRC Handbook of Antibiotic Compounds, CRC Press, U.S.A. (1981)]. UCK14 compounds do not belong to any of these groups according to the classification based on physicochemical properties.

An object of the present invention is to provide compounds which have potent antitumor activity.

SUMMARY OF THE INVENTION

The present invention provides a UCK14 compound having antitumor activity which is represented by formula (I):

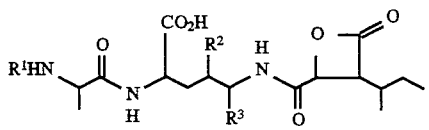

wherein $R^1$ is hydrogen or $-COOC(CH_3)_3$; and $R^2$ and $R^3$ are taken together to form $-CH_2-$, or each $R^2$ and $R^3$ independently is hydrogen,
and a pharmaceutically acceptable salt thereof.

DETAILED DESCRIPTION OF THE INVENTION

The compound represented by formula (I) wherein $R^1$ is hydrogen and $R^2$ and $R^3$ are taken together to form $-CH_2-$ is referred to as UCK14A$_1$; the compound represented by formula (I) wherein $R^1$ is $-COOC(CH_3)_3$ and $R^2$ and $R^3$ are taken together to form $-CH_2-$ is referred to as UCK14A$_2$; and the compound represented by formula (I) wherein $R^1$ is hydrogen and each $R^2$ and $R^3$ independently is hydrogen is referred to as UCK14C.

The pharmaceutically acceptable salts of UCK14 compounds include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate, and organic acid addition salts such as acetate, maleate, fumarate, tartrate, citrate, and methanesulfonate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethylammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The physicochemical properties of UCK14 compounds are shown below.

(i) UCK14A$_1$

Color and form of the substance: White powder

Melting point: 184°–185° C.

Molecular weight: 369

Molecular formula: $C_{17}H_{27}N_3O_6$

Mass spectrum:

FAB mass spectrum: m/z Positive mode (matrix: glycerol); 370 (M+H)$^+$

High resolution FAB mass spectrum: m/z Positive mode (matrix: glycerol); Found; 370.1981 (M+H)$^+$Calculated for $C_{17}H_{28}N_3O_6$; 370.1978

Specific rotation: $[\alpha]_D^{27}=+4.8°$ (c=0.37, $H_2O$)

UV absorption spectrum: End absorption

IR absorption spectrum: $\nu_{max}$ cm$^{-1}$ (KBr); 3261, 3078, 2964, 1834, 1668, 1558, 1456, 1389, 1271, 1111, 914

$^{13}$C-NMR spectrum (125 MHz, $D_2O$): δppm (multiplicity) ;178.5 (s), 173.5 (s), 172.7 (s), 170.8 (s), 71.7 (d), 62.7 (d), 55.7 (d), 50.0 (d), 34.5 (t), 33.6 (d), 29.2 (d), 27.0 (t), 17.3 (q), 16.7 (d), 16.3 (q), 12.1 (t), 11.1 (q)

$^1$H-NMR spectrum (500 MHz, $D_2O$): δppm (integration, multiplicity, coupling constant Hz); 4.93 (1H, d, 4.3), 4.40 (1H, dd, 5.6, 5.6), 4.20 (1H, q, 7.1), 3.91 (1H, dd, 7.4, 4.3), 2.58 (1H, ddd, 7.3, 3.6, 3.6), 2.08 (1H, m), 1.97 (1H, ddd, 14.3, 6.1, 5.6), 1.71 (1H, ddd, 14.3, 8.3, 5.6), 1.63 (3H, d, 7.1), 1.59 (1H, m), 1.37 (1H, m), 1.07 (3H, d, 6.8), 1.02 (1H, m), 0.95 (3H, dd, 7.4, 7.4), 0.90 (1H, m), 0.77 (1H, ddd, 6.5, 6.5, 6.5)

Solubility: Soluble in water, methanol and dimethylsulfoxide (DMSO); insoluble in hexane, chloroform and ethyl acetate Color reaction: Positive to the iodine test, the ninhydrin test and the phosphomolybdic acid/cerium sulfate test Thin layer chromatography: Rf value; 0.5 Thin layer; silica gel TLC (Merck & Co., Inc. ) Developing solvent; butanol:acetic acid:water (71:14:15 v/v/v)

(ii) UCK14A$_2$

Color and form of the substance: White powder

Melting point: 83°–85.° C.

Molecular weight: 469

Molecular formula: $C_{22}H_{35}N_3O_8$

Mass spectrum:

FAB mass spectrum: m/z Positive mode (matrix: NBA); 470 (M+H)$^+$

High resolution FAB mass spectrum: m/z Positive mode (matrix: NBA); Found; 470.2525 (M+H)$^+$Calculated for $C_{22}H_{36}N_3O_8$; 470.2503

Specific rotation: $[\alpha]_D^{28}=-5.1°$ (c=0.78, CHCl$_3$)

UV absorption spectrum: End absorption

IR absorption spectrum: $\nu_{max}$ cm$^{-1}$ (KBr); 3275, 3078 2972, 2933, 1838, 1716, 1662, 1539, 1456, 1392, 1367, 1250, 1169, 1099, 914.

$^{13}$C-NMR spectrum (125 MHz, CDCl$_3$): δppm (multiplicity); 174.4 (s), 173.3 (s), 171.2 (s), 168.7 (s), 155.4 (s), 79.7 (s), 70.3 (d), 63.1 (d), 51.6 (d), 50.0 (d), 33.9 (d), 33.5 (t), 29.4 (d), 28.4 (3C, q), 26.7 (t), 19.3 (q), 17.0 (d), 16.4 (q), 11.1 (q), 10.5 (t)

$^1$H-NMR spectrum (500 MHz, CDCl$_3$): δppm (integration, multiplicity, coupling constant Hz); 9.07 (1H, br), 6.66 (1H, br s), 5.31 (1H, br), 4.87 (1H, m), 4.62 (1H, d, 4.6), 4.40 (1H, m), 3.57 (1H, m), 2.51 (1H, m), 2.48 (1H, m), 1.97 (1H, m), 1.65 (1H, dqd, 13.7, 7.4, 5.4), 1.43 (9H, s), 1.40 (3H, d, 7.0), 1.33 (1H, ddq, 13.7, 7.6, 7.4), 1.15 (1H, ddd, 14.7, 11.1, 5.2), 1.07 (3H, d, 6.7), 0.94 (3H, dd, 7.4, 7.4), 0.90 (1H, m), 0.84 (1H, m), 0.64 (1H, ddd, 6.7, 6.7, 6.7)

Solubility: Soluble in chloroform and ethyl acetate, methanol and dimethylsulfoxide (DMSO); insoluble in hexane, water Color reaction: Positive to the iodine test and the phosphomolybdic acid/cerium sulfate test Thin layer chromatography: Rf value; 0.4 Thin layer; silica gel TLC (Merck & Co., Inc.) Developing solvent; methanol:acetic acid:chloroform (5:1:94 v/v/v)

(iii) UCK14C

Color and form of the substance: White powder
Melting point: 212°–215° C.
Molecular weight: 357
Molecular formula: $C_{16}H_{27}N_3O_6$
Mass spectrum:
FAB mass spectrum: m/z Positive mode (matrix: glycerol); 358 (M+H)$^+$ Negative mode (matrix: glycerol); 356 (M−H)$^-$ High resolution FAB mass spectrum: m/z Negative mode (matrix: glycerol); Found; 356.1838 (M−H)$^-$ Calculated for $C_{16}H_{26}N_3O_6$; 356.1821

Specific rotation: $[\alpha]_D^{27} = -8.1°$ (c=1.2, $H_2O$)
UV absorption spectrum: End absorption
IR absorption spectrum: $\nu_{max}cm^{-1}$ (Kbr); 3388, 3086, 2966, 1834, 1662, 1568, 1412, 1269, 1115, 1016, 903

$^{13}C$-NMR spectrum (100 MHz, $D_2O$): δppm (multiplicity); 179.1 (s), 173.5 (s), 171.1 (s), 170.9 (s), 71.9 (d), 62.8 (d), 56.1 (d), 49.9(d), 39.7 (t), 33.6 (d), 29.5 (t), 27.1 (t), 25.8 (t), 17.3 (q), 16.3 (q), 11.1 (q)

$^1H$-NMR spectrum (400 MHz, $D_2O$): δppm (integration, multiplicity, coupling constant Hz); 4.92 (1H, d, 4.3), 4.16 (1H, dd, 8.1, 5.1), 4.10 (1H, q, 7.1), 3.84 (1H, dd, 7.3, 4.3), 3.30 (2H, t, 6.8), 2.04 (1H, m), 1.81 (1H, m), 1.70 (1H, m), 1.57 (2H, m), 1.55 (3H, d, 7.1), 1.54 (1H, m), 1.33 (1H, m), 1.03 (3H, d, 6.8), 0.90 (3H, dd, 7.4, 7.4)

Solubility: Soluble in chloroform, ethyl acetate, methanol and dimethylsulfoxide (DMSO); insoluble in hexane and water Color reaction: Positive to the iodine test, the ninhydrin test and the phosphomolybdic acid/cerium sulfate test Thin layer chromatography: Rf value; 0.5 Thin layer; silica gel TLC (Merck & Co., Inc.) Developing solvent; butanol:acetic acid:water (71:14:15 v/v/v)

The biological activity of UCK14 compounds is described below by Test Example.

Test Example

Growth inhibition against human epidermoid carcinoma A431 cells and human pancreatic carcinoma PSN-1 cells Human epidermoid carcinoma A431 cells (ATCC CRL 1555) were suspended in Dulbecco's modified Eagle's medium (Nissui Pharmaceutical Co., Ltd.) supplemented with 10% fetal bovine serum (Filtron), and human pancreatic carcinoma PSN-1 cells [Biochem. Biophys. Res. Commun. 140, 167 (1986)] were suspended in RPMI-1640 medium (Gibco BRL) supplemented with 5% fetal bovine serum (Filtron). Each cell suspension was put into wells of a 96-well microtiter plate (#167008, Nunc) in an amount of $3\times10^3$ cells/well, followed by preincubation in a 5% $CO_2$-incubator at 37° C. for 24 hours. Then, 5mM solutions of $UCK14A_1$, $UCK14A_2$ and UCK14C were diluted stepwise and the resulting solutions were respectively added to the wells in an amount of 50 μl/well (highest final concentration: 1 mM). The cells were cultured in the 5% $CO_2$-incubator at 37° C. for 72 hours. Five hours before the end of culturing, 50 μl of a solution of MTT [3-(4,5-dimethylthiazo-2-yl)-2,5-diphenyltetrazolium bromide (Sigma Chemical Co., Ltd.)] in the medium (final concentration: 1 mg/ml) was added to each well. After the completion of culturing, DMSO was added to the wells in an amount of 150 μl/well, followed by vigorous stirring with a plate mixer to completely dissolve crystals of MTT-formazan. The absorbance at 550 nM was measured by using a microplate reader MTP-32 (Corona Electric Co., Ltd.), and the cell growth inhibiting activity was expressed in terms of 50% growth inhibitory concentration ($IC_{50}$). The result is shown in Table 1.

TABLE 1

| Compound | $IC_{50}$ (μM) | |
|---|---|---|
| | A431 | PSN-1 |
| $UCK14A_1$ | 25.2 | 16.1 |
| $UCK14A_2$ | 53.3 | 22.9 |
| UCK14C | 696 | 591 |

The process for producing UCK14 compounds is described below.

$UCK14A_1$ and UCK14C can be obtained by culturing in a medium a microorganism belonging to the genus Streptomyces and having the ability to produce UCK14 compounds, allowing UCK14 compounds to accumulate in the culture, and recovering $UCK14A_1$ and UCK14C from the culture. $UCK14A_2$ can be obtained by chemically modifying $UCK14A_1$.

As the UCK14-compound-producing strains of the present invention, any strains which belong to the genus Streptomyces and have the ability to produce UCK14 compounds can be used. In addition, any mutants of such strains which are obtained by various artificial mutation methods such as UV irradiation, X ray irradiation and treatment with mutagens or by spontaneous mutation may also be used in the present invention, insofar as they have the ability to produce UCK14 compounds. A typical example of a suitable strain is Streptomyces sp. UCK14 strain which was newly isolated from soil by the present inventors.

The morphological, cultural, physiological and chemotaxonomic characteristics of Streptomyces sp. UCK14 strain are described below.

1. Morphological characteristics
   1) Hyphae
   Formation of aerial hyphae: Observed
   Fragmentation and motility of aerial hyphae: Not observed
   Fragmentation and motility of substrate hyphae: Not observed
   2) Spores
   Formation and location of spores: Formed on the aerial hyphae
   Formation and location of sporangia: Not observed
   Number of spores in chain formed at the end of the sporophore: 10 or more
   Form of spore chains: Spiral
   Characteristics of spores: Surface; Smooth Form and size; Short rod, ca. 0.8–0.9 μm×1.0–1.2 μm Motility of spores and existence of flagella; Not observed
   3) Others
   Chlamydospores; Not observed
   Synnemata; Not observed
   Pseudosporangia; Not observed
   Branching mode of hyphae; Simple branching
2. Cultural characteristics The strain UCK14 shows moderate or good growth on synthetic media and natural media which are generally used. The color of the substrate hyphae is yellow to red. Formation of soluble brown pigment was observed on some of the culture media.

The cultural characteristics such as growth and color of UCK14 strain on various agar media observed after culturing at 28° C. for 14 days are shown below. The color names were given according to the Color Harmony Manual (Container Corporation of America, 4th edition, 1958).

1) Sucrose—nitrate agar medium
Growth; Poor
Color of substrate hyphae; Rose beige (4ge)
Formation and color of aerial hyphae; Poor, rose beige (4ge)
Soluble pigment; None 2) Glucose—asparagine agar medium
Growth; Good
Color of substrate hyphae; Covert tan (2ge)-beige (3ge)
Formation and color of aerial hyphae; Abundant, rose beige (4ge)-fawn (4ig)
Soluble pigment; None 3) Glycerol—asparagine agar medium
Growth; Good
Color of substrate hyphae; Camel (3ie)-light brown (31g)
Formation and color of aerial hyphae; Abundant, rose beige (4ge)
Soluble pigment; Formed only a little (yellow)

4) Starch—inorganic salts agar medium
Growth; Good
Color of substrate hyphae; Light beige (3ec)-camel (3ie)
Formation and color of aerial hyphae; Abundant, fawn (4ig)
Soluble pigment; Formed (ocher)

5) Tyrosine agar medium
Growth; Good
Color of substrate hyphae; Light tan (3gc)-camel (3ie)
Formation and color of aerial hyphae; Abundant, white (a)-rose beige (4ge)
Soluble pigment; None 6) Nutrient agar medium
Growth; Poor
Color of substrate hyphae; Light mustard tan (2ie)
Formation and color of aerial hyphae; Formed little
Soluble pigment; None 7) Yeast—malt agar medium
Growth; Good
Color of substrate hyphae; Cinnamon (31e)
Formation and color of aerial hyphae; Abundant, rose beige (4ge)
Soluble pigment; Formed (brown)

8) Oatmeal agar medium
Growth; Good
Color of substrate hyphae; Camel (3ie)
Formation and color of aerial hyphae; Abundant, rose beige (4ge)
Soluble pigment; Formed (ocher)

3. Physiological characteristics

The physiological characteristics of UCK14 strain are shown below. The result of 1) was obtained after 14 days of culturing and the results of 2)–6) were obtained after 2 to 3 weeks of culturing at 28° C.

1) Growth temperature range; 16.0°–49.0° C.
2) Liquefaction of gelatin; Positive
3) Hydrolysis of starch; Positive
4) Coagulation and peptonization of skim milk powder; Peptonized
5) Production of melanin-like pigment
   (i) Peptone-yeast-iron agar medium; Negative
   (ii) Tyrosine agar medium; Negative
6) Assimilability of carbon sources As the basis medium, Pridham Gottlieb agar medium was used. In the following, + indicates that the strain utilized the carbon source, − indicates that the strain did not utilize the carbon source, and W indicates that it is not clear whether the strain utilized the carbon source.

L-Arabinose; +
D-Xylose; +
D-Glucose; +
Sucrose; W
Raffinose; W
D-Fructose; +
Rhamnose; −
Inositol; W
D-Mannitol; W 4. Chemotaxonomic characteristics
   1) Configuration of diaminopimelic acid in whole-cell hydrolyzate; LL-form
   2) Major quinone component of cellular lipid; MK-9 (H8)

The strain is classified in the genus Streptomyces among actinomycetes in view of its characteristics: that spore chains are formed on the aerial hyphae; that it belongs to the Type I cell wall group (LL-diaminopimelic acid, glycine); and that the major quinone component is octahydrogenated menaquinone 9 [MX-9 ($H_8$)].

The strain was named Streptomyces sp. UCK14 and was deposited with the National Institute of Bioscience and Human-Technology, Agency of Industrial Science and Technology on Aug. 22, 1995 with accession number FERM BP-5203.

For the culturing of the UCK14-compound-producing strains used in the present invention, conventional methods for culturing actinomycetes are generally employed. As the medium, either a synthetic medium or a natural medium may be used insofar as it appropriately contains carbon sources, nitrogen sources and inorganic substances which can be assimilated by the strains employed and the growth- and production-promoting substances required.

As the carbon sources, glucose, starch, dextrin, mannose, fructose, sucrose, lactose, xylose, arabinose, mannitol, molasses, etc. can be used alone or in combination. In addition, hydrocarbons, alcohols, organic acids, etc. may also be used according to the assimilability of the microorganism employed.

As the nitrogen sources, ammonium chloride, ammonium nitrate, ammonium sulfate, sodium nitrate, urea, peptone, meat extract, yeast extract, dry yeast, corn steep liquor, soybean powder, casamino acid, etc. can be used alone or in combination.

If necessary, inorganic salts such as sodium chloride, potassium chloride, magnesium sulfate, calcium carbonate, potassium dihydrogen phosphate, ferrous sulfate, calcium chloride, manganese sulfate, zinc sulfate, and copper sulfate may be added. In addition, trace ingredients that promote the growth of the strain employed and the production of UCK14 compounds may also be added to the medium.

As the method of culturing, liquid culture, especially submerged stirring culture, is preferably employed. Culturing is carried out at 16° to 37° C., preferably 25° to 32° C., and at pH 4 to 10, preferably 6 to 8. In general, culturing is completed in 1 to 7 days. In order to adjust the pH of the medium, aqueous ammonia, ammonium carbonate solution, etc. are used.

UCK14 compounds are produced and accumulated in the culture broth and the microbial cells. When the amount of the product in the culture reaches the maximum, the culturing is discontinued.

For the isolation and purification of UCK14 compounds from the culture, an ordinary method for isolating a microbial metabolite from the culture, e.g. extraction and various kinds of chromatography can be utilized. The compounds can also be isolated by chemical modification of a crude product and regeneration.

For example, the culture is separated into culture filtrate and microbial cells by filtration. The microbial cells are extracted with a solvent such as chloroform or acetone. Then, the extract is mixed with the culture filtrate, and the resulting mixture is passed through a column of polystyrene adsorbent such as Diaion HP20 (Mitsubishi Chemical Corporation) to adsorb the active substance, followed by elution with a solvent such as methanol or acetone. The eluate is concentrated, and the concentrate is subjected to ODS column chromatography, high performance liquid chromatography, silica gel column chromatography, and the like to give UCK14 compounds. During the culture and purification steps, UCK14 compounds can be traced by silica gel thin layer chromatography, followed by detection with iodine reagent.

UCK14 compounds and pharmaceutically acceptable salts thereof can be administered as such or as pharmaceutical compositions either orally or parenterally. The forms of pharmaceutical compositions include tablets, pills, powders, granules, capsules, suppositories, injections and drips.

These pharmaceutical compositions can be prepared by generally known methods. For example, the compositions may be formulated to contain various excipients, lubricants, binders, disintegrators, suspending agents, isotonizing agents, emulsifying agents, absorption accelerators, and the like.

Examples of the carriers to be used in the pharmaceutical compositions are water, distilled water for injection, physiological saline, glucose, fructose, sucrose, mannitol, lactose, starch, corn starch, potato starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters. These carriers are appropriately selected depending on the preparation form.

The dose will vary depending on the desired therapeutic effect, the mode of administration, the administration period, the age and weight of a patient, etc. However, it is generally preferred to administer Compound (I) or its pharmaceutically acceptable salts in a dose of 0.1 to 100 mg/kg per day in 3 to 4 divisional administrations.

Certain embodiments of the invention are illustrated in the following Examples.

EXAMPLE 1

Streptomyces sp. UCK14 strain was used as the seed strain. The strain was inoculated into 300 ml of a seed medium having the following composition in a 2l-Erlenmeyer flask, and cultured with shaking (rotation: 200 rpm) at 28° C. for 48 hours.

Composition of the seed medium: 10 g/l glucose, 10 g/l soluble starch, 5 g/l Bacto-tryptone (Difco Laboratories Inc.), 5 g/l yeast extract, 3 g/l meat extract, and 0.5 g/l magnesium phosphate (pH 7.2 before sterilization)

The resulting seed culture was transferred into 18l of a fermentation medium having the following composition in a 30 l-jar fermentor in an amount of 5% (by volume) of the fermentation medium and culturing was carried out at 25° C. with stirring and aeration (rotation: 300 rpm, aeration: 18 l/min.).

Composition of the fermentation medium: 25 g/l glycerol, 25 g/l glucose, 15 g/l dry yeast, 0.5 g/l $KH_2PO_4$, and 0.5 g/l $Mg_3(PO_4)^2 \cdot 8H_2O$ (pH 7.0 before sterilization, adjusted with NaOH)

Culturing was carried out for 96 hours without controlling the pH of the medium. The resulting culture was separated into culture filtrate and microbial cells by filtration. The filtrate was passed through a column of Diaion HP-20 to adsorb the active substance. After impurities were eluted with methanol-water (3:7 v/v), the active substance was eluted with methanol-water (4:6 v/v) and methanol-water (5:5 v/v). The active fraction was concentrated, and the concentrate was passed through a column of Diaion HP-20SS to adsorb the active substance. After impurities were eluted with methanol-water (2:8 v/v), the active substance was eluted with methanol-water (3:7 v/v) and methanol-water (4:6 v/v). The active fraction was concentrated, and the concentrate was subjected to ODS column chromatography to adsorb the active substance. After impurities were eluted with methanol-water (2:8 v/v), the active substance was eluted with methanol-water (3:7 v/v) and methanol-water (4:6 v/v). The active fraction was concentrated, and the concentrate was subjected to high performance liquid chromatography (HPLC), followed by development with 0–80% aqueous methanol. The eluted active fraction was concentrated, and the concentrate was subjected to silica gel column chromatography. Development was carried out with butanol-acetic acid-water (400:1:1–400:32:32 v/v/v), whereby a fraction containing crude $UCK14A_1$ as a main component and a fraction containing UCK14C were obtained. Concentration of the fraction containing UCK14C gave 20 mg of UCK14C as a white solid.

EXAMPLE 2

Formation of $UCK14A_2$ by t-butoxycarbonylation

The fraction containing crude $UCK14A_1$ as a main component obtained in Example 1 (20 mg) was dissolved in 0.5 ml of 50% aqueous tetrahydrofuran, and the solution was adjusted to pH 7.5 by addition of saturated $NaHCO_3$. To the solution was added 10 mg of di-t-butyl dicarbonate, followed by stirring at room temperature for one hour. After being adjusted to pH 4 with 1N aqueous solution of hydrochloric acid, the reaction mixture was extracted with chloroform, and the extract was dried over $Na_2SO_4$ and concentrated to dryness. The obtained product was dissolved in chloroform and the solution was subjected to silica gel column chromatography. Development was carried out with chloroform-methanol-acetic acid (200:1:0.1–200:4:0.4 v/v/v) to give 17 mg of $UCK14A_2$ as a white solid.

EXAMPLE 3

Formation of $UCK14A_1$ by de-t-butoxycarbonylation $UCK14A_2$ (7 mg) was dissolved in 0.5 ml of dichloromethane, and 0.1 ml of trifluoroacetic acid was added to the solution, followed by stirring at room temperature for 3 hours. The reaction mixture was concentrated to dryness and the concentrate was dissolved in water. The solution was subjected to ODS column chromatography, and elution was carried out with methanol-water (5:5 v/v) to give 5 mg of $UCK14A_1$ as a white solid.

What is claimed is:

1. A UCK14 compound which is represented by formula (I):

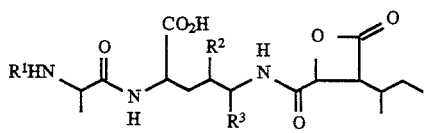 (I)

wherein $R^1$ is hydrogen or —COOC(CH$_3$)$_3$; and $R^2$ and $R^3$ are taken together to form —CH$_2$—, or each $R^2$ and $R^3$ independently is hydrogen, or a pharmaceutically acceptable salt thereof.

2. The UCK14 compound according to claim 1, wherein $R^1$ is hydrogen, and $R^2$ and $R^3$ are taken together to form —CH$_2$—.

3. The UCK14 compound according to claim 1, wherein $R^1$ is —COOC(CH$_3$)$_3$, and $R^2$ and $R^3$ are taken together to form —CH$_2$—.

4. The UCK14 compound according to claim 1, wherein each $R^1$, $R^2$ and $R^3$ are hydrogen.

5. A pharmaceutical composition comprising a pharmaceutically acceptable carrier and as an active ingredient, an effective amount of the compound as defined by claim 1.

* * * * *